US009844222B2

(12) United States Patent
Verma et al.

(10) Patent No.: US 9,844,222 B2
(45) Date of Patent: Dec. 19, 2017

(54) METAL NANOPARTICLES-DOPED ANTIBACTERIAL AGENTS AND METHODS OF PREPARATION AND USE

(71) Applicant: INDIAN INSTITUTE OF TECHNOLOGY KANPUR, Kanpur (IN)

(72) Inventors: Nishith Verma, Kanpur (IN); Ashutosh Sharma, Kanpur (IN); Prateek Khare, Kanpur (IN)

(73) Assignee: INDIAN INSTITUTE OF TECHNOLOGY KANPUR, Kanpur (IN)

( * ) Notice: Subject to any disclaimer, the term of this patent is extended or adjusted under 35 U.S.C. 154(b) by 141 days.

(21) Appl. No.: 14/462,580

(22) Filed: Aug. 19, 2014

(65) Prior Publication Data

US 2015/0056260 A1 Feb. 26, 2015

(30) Foreign Application Priority Data

Aug. 20, 2013 (IN) .......................... 2463/DEL/2013

(51) Int. Cl.
*A01N 59/20* (2006.01)
*A01N 59/16* (2006.01)
*C02F 1/50* (2006.01)

(52) U.S. Cl.
CPC ............ *A01N 59/20* (2013.01); *A01N 59/16* (2013.01); *C02F 1/505* (2013.01); *C02F 2305/08* (2013.01)

(58) Field of Classification Search
None
See application file for complete search history.

(56) References Cited

U.S. PATENT DOCUMENTS

| | | | |
|---|---|---|---|
| 4,427,793 A | 1/1984 | Reed et al. | |
| 4,772,635 A | 9/1988 | Mitschker et al. | |
| 4,970,189 A * | 11/1990 | Tachibana | C04B 35/528 502/182 |
| 5,583,162 A | 12/1996 | Li et al. | |
| 6,171,489 B1 | 1/2001 | Ballard et al. | |
| 7,422,759 B2 | 9/2008 | Kepner et al. | |
| 7,449,236 B2 | 11/2008 | Lanphere et al. | |
| 7,963,720 B2 | 6/2011 | Hoag et al. | |
| 2011/0124492 A1 | 5/2011 | Loukine et al. | |

OTHER PUBLICATIONS

El-Aassar, A. H. M.; Said, M. M.; Abdel-Gawad, A.; Shawky, H. A. Using silver nanoparticles coated on activated carbon granules in columns for microbiological pollutants water disinfection in Abu Rawash area, Great Cairo, Egypt. Australian Journal of Basic and Applied Sciences, 7(1): 422-432, 2013.*

Moreno-Pirajan, J. C.; Tirano, J.; Salamanca, B.; Giraldo, L. Activated carbon modified with copper for adsorption of propanethiol. International Journal of Molecular Sciences, 2010, 11, 927-942.*
Kumar, V.; Talrej, N.; Deva, D.; Sankararamakrishnan, N.; Sharma, A.; Verma, N. Development of bi-metal doped micro and nano multi-functional polymeric adsorbents for the removal of fluoride and arsenic (V) from wastewater. Desalination, 282, 2011, 27-38.*
P. Mondal et al., "Effects of Adsorbent Dose, Its Particle Size and Initial Arsenic Concentration on the Removal of Arsenic, Iron and Manganese from Simulated Ground Water by Fe3+ Impregnated Activated Carbon", Journal of Hazardous Materials, Feb. 11, 2008, pp. 695-702, vol. 150, Issue 3.
M. Agarwal et al., "Deflouridation of Water Using Amended Clay", Journal of Cleaner Production, 2003, pp. 439-444, vol. 11.
G. Alagumuthu et al., "Equilibrium and Kinetics of Adsorption of Fluoride Onto Zirconium Impregnated Cashew Nut Shell Carbon", Chemical Engineering Journal, 2010, pp. 451-457, vol. 158.
Richard J. Ansell et al., "Magnetic Molecularly Imprinted Polymer Beads for Drug Radioligand Binding Assay", Analyst, Jul. 1998, pp. 1611-1616, vol. 123, No. 7.
Mohammad Badruzzaman et al., "Intraparticle Diffusion and Adsorption of Arsenate Onto Granular Ferric Hydroxide (GFH)", Water Research, 2004, pp. 4002-4012, vol. 38.
Lucy M. Camacho et al., "Adsorption Equilibrium and Kinetics of Fluoride on Sol-Gel-Derived Activated Alumina Adsorbents", Journal of Colloid and Interface Science, 2010, pp. 307-313, vol. 349.
Vivek Singh Chauhan et al., "Investigations on Activated Alumina Based Domestic Defluoridation Units", Journal of Hazardous Materials, 2007, pp. 103-108, vol. B139.
Nan Chen et al., "Preparation and Characterization of Porous Granular Ceramic Containing Dispersed Aluminum and Iron Oxides as Adsorbents for Fluoride Removal from Aqueous Solution", Journal of Hazardous Materials, 2011, pp. 863-868, vol. 186.
A.A.M. Daifullah et al., "Adsorption of Fluoride in Aqueous Solutions Using KMnO4-Modified Activated Carbon Derived from Steam Pyrolysis of Rice Straw", Journal of Hazardous Materials, 2007, pp. 633-643, vol. 147.
Son Van Dang et al., "Removal of Arsenic from Synthetic Groundwater by Adsorption Using the Combination of Laterite and Iron-Modified Activated Carbon", Journal of Water and Environment Technology, 2008, pp. 43-54, vol. 6, No. 1.
Nigamananda Das et al., "Defluoridation of Drinking Water Using Activated Titanium Rich Bauxite", Journal of Colloid and Interface Science, 2005, pp. 1-10, vol. 292.
Ratan Das et al., "Preparation and Antibacterial Activity of Silver Nanoparticles", Journal of Biomaterials and Nanobiotechnology, 2011, pp. 472-475, vol. 2.
K K R Datta et al.,"Synthesis of Agarose-Metal/Semiconductor Nanoparticles Having Superior Bacteriocidal Activity and Their Simple Conversion to Metal-Carbon Composites", J. Chem. Sci., Nov. 2008, pp. 579-586, vol. 120, No. 6, Indian Academy of Sciences.
Xiao Bin Ding et al., "Preparation of Thermosensitive Magnetic Particles by Dispersion Polymerization", Reactive & Functional Polymers, 1998, pp. 11-15, vol. 38.

(Continued)

*Primary Examiner* — Jessica Worsham
(74) *Attorney, Agent, or Firm* — Turk IP Law, LLC

(57) ABSTRACT

A metal nanoparticles-doped porous carbon bead having an average size of about 0.4 millimeter (mm) to about 0.6 mm is provided. The metal nanoparticles-doped porous carbon bead is doped with silver, copper, or combinations thereof.

6 Claims, 4 Drawing Sheets

(56) References Cited

OTHER PUBLICATIONS

Qing Ling Feng et al. "Antibacterial Effects of Ag-HAp Thin Films on Alumina Substrates", Thin Solid Films, 1998, pp. 214-219, vol. 335, Issues 1-2.
Subhashini Ghorai et al., "Equilibrium, Kinetics and Breakthrough Studies for Adsorption of Fluoride on Activated Alumina", Separation and Purification Technology, Apr. 2005, pp. 265-270, vol. 42, Issue 3.
Subhashini Ghorai et al., Investigations on the Column Performance of Fluoride Adsorption by Activated Alumina in a Fixed Bed, Chemical Engineering Journal, 2004, pp. 165-173, vol. 98, No. 1-2.
V. Gopal et al., "Equilibrium, Kinetic and Thermodynamic Studies of Adsorption of Fluoride Onto Plaster of Paris", Journal of Hazardous Materials, 2007, pp. 98-105, vol. 141.
Maribel G. Guzman et al., "Synthesis of Silver Nanoparticles by Chemical Reduction Method and Their Antibacterial Activity", International Journal of Chemical and Biological Engineering, 2009, pp. 104-111, vol. 2, No. 3.
Hye-Jin Hong et al., "Removal of Arsenate, Chromate and Ferricyanide by Cationic Surfactant Modified Powdered Activated Carbon", Desalination, 2008, pp. 221-228, vol. 223, No. 1-3.
Min Jang et al., "Preloading Hydrous Ferric Oxide into Granular Activated Carbon for Arsenic Removal", Environ. Sci. Technol., 2008, pp. 3369-3375, vol. 42, No. 9.
Young Hwan Kim et al. "Preparation and Characterization of the Antibacterial Cu Nanoparticle Formed on the Surface of SiO2 Nanoparticles", J. Phys. Chem. B, 2006, pp. 24923-24928, vol. 110, No. 49.
Hyeyoung Kong et al., "Antibacterial Properties of Novel Poly(methyl methacrylate) Nanofiber Containing Silver Nanoparticles", Langmuir, 2008, pp. 2051-2056, vol. 24, No. 5.
Vikas Kumar et al., "Development of Bi-Metal Doped Micro- and Nano Multi-Functional Polymeric Adsorbents for the Removal of Fluoride and Arsenic(V) from Wastewater", Desalination, 2011, pp. 27-38, vol. 282.
Veronique Lenoble et al., "Arsenic Removal by Adsorption on Iron(III) Phosphate", Journal of Hazardous Materials, 2005, pp. 262-268, vol. B123.
H. Lounici et al., "Fluoride Removal with Electro-Activated Alumina", Desalination, 2004, pp. 287-293, vol. 161.
Yue Ma et al., "Characteristics and Defluoridation Performance of Granular Activated Carbons Coated with Manganese Oxides", Journal of Hazardous Materials, 2009, pp. 1140-1146, vol. 168.
Sibdas Singha Mahapatra et al., "Silver Nanoparticle in Hyperbranched Polyamine: Synthesis, Characterization and Antibacterial Activity", Materials Chemistry and Physics, 2008, pp. 1114-1119, vol. 112.
Muhammad Aslam Malana et al, "Adsorption Studies of Arsenic on Nano Aluminium Doped Manganese Copper Ferrite Polymer (MA, VA, AA) Composite: Kinetics and Mechanism", Chemical engineering Journal, Jun. 2011, pp. 721-727, vol. 172.
Shihabudheen M. Maliyekkal et al., "Manganese-Oxide-Coated Alumina: A Promising Sorbent for Defluoridation of Water", Water Research, 2006, pp. 3497-3506, vol. 40.
Luiz Claudio De Santa Maria et al., "Preparation of Composite Materials Containing Iron in a Cross-Linked Resin Host based on Styrene and Divinylbenzene", European Polymer Journal, 2003, pp. 843-846, vol. 39 \.
Amitava Mukherjee et al., "Arsenic Contamination in Groundwater: A Global Perspective with Emphasis on the Asian Scenario", J Health Popul. Nutr., Jun 2006, pp. 142-163, vol. 24, No. 2.
Kristopher Page et al., "Titania and Silver-Titania Composite Films on Glass-Potent Antimicrobial Coatings", Journal of Materials Chemistry, 2007, pp. 95-104 , vol. 17, No. 1.
Sangphil Park et al., "Preparation of Silver Nanoparticle-Containing Semi-Interpenetrating Network Hydrogels Composed of Pluronic and Poly(Acrylamide) with Antibacterial Property", Journal of Industrial and Engineering Chemistry, 2011, pp. 293-297, vol. 17.
Dang Viet Quang et al. "Preparation of Silver Nanoparticle Containing Silica Micro Beads and Investigation of their Antibacterial Activity", Applied Surface Science, 2011, pp. 6963-6970, vol. 257, Issue 15.
Sunil Rana et al., "Synthesis of Magnetic Beads for Solid Phase Synthesis and Reaction Scavenging", Tetrahedron Letters, 1999, vol. 40, pp. 8137-8140, vol. 40.
Jayesh P. Ruparelia et al., "Strain Specificity in Antimicrobial Activity of Silver and Copper Nanoparticles", Acta Biomaterialia, 2008, pp. 707-716, vol. 4, No. 3.
Ivan Sondi et al., "Silver Nanoparticles as Antimicrobial Agent: A Case Study on *E. coli* as a Model for Gram-Negative Bacteria", Journal of Colloid and Interface Science, 2004, pp. 177-182, vol. 275, Issue 1.
R. Sai Sathish et al., "Equilibrium and Kinetic Studies for Fluoride Adsorption from Water on Zirconium Impregnated Coconut Shell Carbon", Separation Science and Technology, Mar. 16, 2007, pp. 769-788, vol. 42, No. 4.
M. G. Sujana et al., "Characterization and Fluoride Uptake Studies of Nano-Scale Iron Oxide-Hydroxide Synthesized by Microemulsion Method", International Journal of Engineering, Science and Technology, 2010, pp. 1-12, vol. 2, No. 8.
Sushree Swarupa Tripathy et al., "Removal of Fluoride from Drinking Water by Adsorption Onto Alum-impregnated Activated Alumina", Separation and Purification Technology, 2006, pp. 310-317, vol. 50.
Linfeng Wu et al., "Removal of Trichloroethylene from Water by Cellulose Acetate Supported Bimetallic Ni/Fe Nanoparticles", Chemosphere, 2006, pp. 285-292, vol. 63.
Jixin Yang et al., "A Novel Synthetic Route to Metal-Polymer Nanocomposites by in Situ Suspension and Bulk Polymerizations", European Polymer Journal, 2008, pp. 1331-1336, vol. 44.
Chaocan Zhang et al., "Synthesis and Adsorption Properties of Magnetic Resin Microbeads with Amine and Mercaptan as Chelating Groups", Journal of Applied Polymer Science, 2001, pp. 1587-1592, vol. 82.

\* cited by examiner

US 9,844,222 B2

METAL NANOPARTICLES-DOPED ANTIBACTERIAL AGENTS AND METHODS OF PREPARATION AND USE

CROSS-REFERENCE TO RELATED APPLICATIONS

This application claims priority to Indian Patent Application 2463/DEL/2013, filed on Aug. 20, 2013. The Indian Patent Application, including any appendices or attachments thereof, is incorporated by reference herein in its entirety.

BACKGROUND

Microbial contamination of water poses a threat to public health. While many contaminants in water including heavy metals and dissolved solids can be removed at the water source, control of bacteria in potable water requires efficient water purifiers. Several chemical agents and physical treatments, such as ozone, chlorine and its derivatives, ultraviolet light and radiation, are used to inhibit bacterial contamination in water. However, residual agents in treated water can have unwanted side effects.

Antibacterial properties of metal nanoparticles such as silver (Ag) and copper (Cu) nanoparticles are known. The antibacterial properties of the metal nanoparticles are attributed to relatively small size and high surface to volume ratio of the nanoparticles that allows them to interact closely with bacteria. Metal nanoparticles with antibacterial properties can be coated on surfaces that may be used for a variety of applications such as in medical instruments and water treatment and food processing devices. However, synthesis of metal nanoparticles such as silver nanoparticles can be substantially expensive. Moreover, it is difficult to achieve a uniform dispersion of the metal nanoparticles in a substrate. The materials with non-uniform dispersion of metal nanoparticles may not be effective in controlling and/or inhibiting growth of bacteria in a medium such as water.

SUMMARY

The foregoing summary is illustrative only and is not intended to be in any way limiting. In addition to the illustrative aspects, embodiments, and features described above, further aspects, embodiments, and features will become apparent by reference to the drawings and the following detailed description.

Briefly, in accordance with one aspect, a metal nanoparticles-doped porous carbon bead having an average size of about 0.4 millimeter (mm) to about 0.6 mm is provided. The metal nanoparticles-doped porous carbon bead is doped with silver, copper, or combinations thereof.

In accordance with another aspect, a method of forming a metal nanoparticles-doped carbon bead is provided. The method includes preparing a reaction mixture of at least one monomer, at least one solvent and at least one catalyst for forming a polymer bead. The method includes adding one or more metallic salts to the reaction mixture to form a metal nanoparticles-doped polymer bead. The method also includes carbonizing and activating the metal nanoparticles-doped polymer bead to form a porous metal-oxide doped activated carbon bead. The method further includes reducing the metal-oxide doped activated carbon bead to form a metal nanoparticles-doped porous carbon bead.

In accordance with another aspect, an antibacterial agent for inhibiting bacteria is provided. The antibacterial agent includes one or more metal nanoparticles-doped porous carbon beads. The one or more metal nanoparticles-doped porous carbon beads are doped with silver, copper, or combinations thereof.

In accordance with another aspect, a method of inhibiting bacteria in a sample is provided. The method includes contacting the sample with an antibacterial agent having one or more metal nanoparticles-doped porous carbon beads. The one or more porous carbon beads are doped with silver, copper, or combinations thereof. The growth of bacteria in the sample is controlled by the one or more metal nanoparticles-doped porous carbon bead.

DETAILED DESCRIPTION

Figure 1:
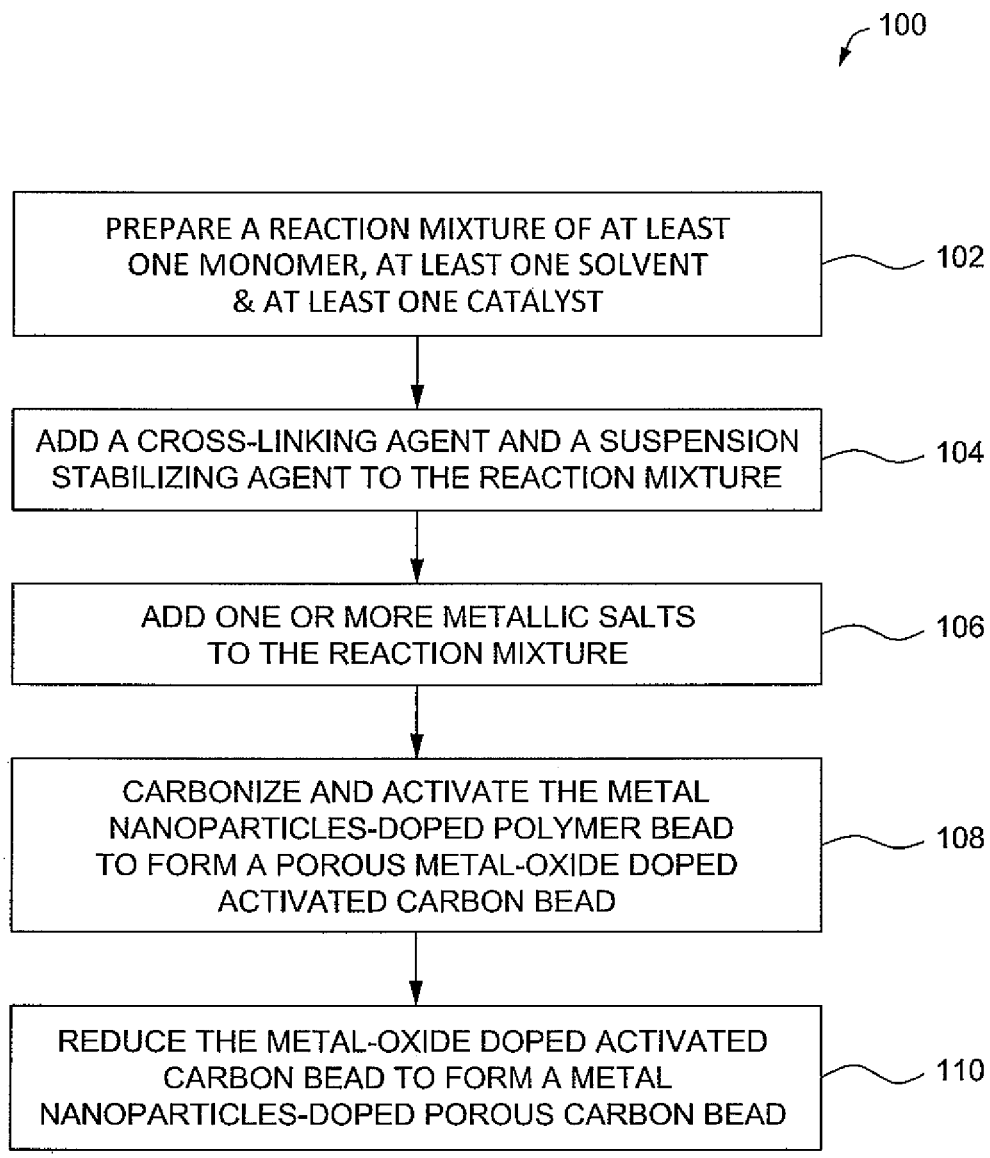
FIG. 1 is an example flow diagram of an embodiment of a method of forming a metal nanoparticles-doped porous carbon bead.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

It will also be understood that any compound, material or substance which is expressly or implicitly disclosed in the specification and/or recited in a claim as belonging to a group or structurally, compositionally and/or functionally related compounds, materials or substances, includes individual representatives of the group and all combinations thereof. While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

Example embodiments are generally directed to techniques of forming metal nanoparticles-doped porous carbon beads that can be utilized as antibacterial agents for water purification. The technique provides micron size metal nanoparticles-doped porous carbon beads that are formed using a suspension polymerization reaction. The metals such as copper and silver are incorporated in-situ into the beads and such beads are activated and carbonized to form metal nanoparticles-doped porous carbon beads. The beads have substantially large surface area with loading of metal nanoparticles in their micro-mesopores so that the metal nanoparticles in the beads are accessible to the bacteria. Such materials function as antibacterial agents and can be used for effectively controlling growth of bacteria in water.

Referring now to FIG. 1, an example flow diagram 100 of forming a metal nanoparticles-doped porous carbon bead is illustrated. At block 102, a reaction mixture of at least one monomer, at least one solvent and at least one catalyst is prepared for forming a polymer bead. In this example, the polymer bead is formed by a suspension polymerization reaction. In some embodiments, only one type of monomer is used. In some embodiments, two different monomers are used. In yet another embodiment, more than two different monomers are used. Examples of the at least one monomer include, but are not limited to, alcohol, aromatic alcohol, phenol, vinyl benzyl alcohol, cresol, butylphenol, non-aromatic methyl methacrylate (MMA), or combinations thereof.

Examples of the at least one solvent include, but are not limited to, formaldehyde, acetaldehyde, paraldehyde, glyoxal, or combination thereof. In some embodiments, the catalyst is a base catalyst. Examples of the at least one catalyst include, but are not limited to, triethylamine (TEA), sodium hydroxide, barium hydroxide, dimethylamine, or combinations thereof.

In this embodiment, the at least one monomer, the at least one solvent, and the at least one catalyst are heated to form a heated reaction mixture. In some embodiments, the at least one monomer, at least one solvent, and at least one catalyst are mixed at a temperature of about 20° C. to about 30° C. until the mixture is homogenous. The mixture is then heated to a temperature of about 100° C. The heating rate for the mixture is maintained at about 1° C. per minute to about 5° C. per minute. Specific examples of heating rate include about 1° C. per minute, about 2° C. per minute, about 3° C. per minute, about 4° C. per minute, about 5° C. per minute and ranges between any two of these values (including endpoints).

In some embodiments, the heated mixture is contacted with an aqueous solution. In some embodiments, the aqueous solution is water. In some embodiments, the mixture is continued to be mixed for a time period of about 10 minutes to about 60 minutes. Specific examples of the time period of mixing include about 10 minutes, about 20 minutes, about 30 minutes, about 40 minutes, about 50 minutes, about 60 minutes and ranges between any two of these values (including endpoints).

At block 104, a cross-linking agent is added to the reaction mixture to form a cross-linked reaction mixture. Examples of the cross-linking agent include, but are not limited to, hexamethylenetetramine (HMTA or hexamine), triethylene diamine and sulfuric acid, or any combination thereof. After contacting the reaction mixture with the cross-linking agent the mixture is heated until the temperature reaches a value of about 70° C. to about 110° C. Specific examples of the heating temperature include about 70° C., about 80° C., about 90° C., about 100° C., about 110° C. and ranges between any two of these values (including endpoints). In some examples, the temperature is increased at a heating rate of about 1° C. per minute to about 5° C. per minute until a target temperature is achieved. Specific examples of the heating rate include about 1° C. per minute, about 2° C. per minute, about 3° C. per minute, about 4° C. per minute, about 5° C. per minute and ranges between any two of these values (including endpoints).

In this embodiment, the cross-linked reaction mixture is contacted with a suspension stabilizing agent. Examples of the suspension stabilizing agent include, but are not limited to, PVA (polyvinyl alcohol), gum acacia powder (GAP), polyvinyl pyrrolidone, or combinations thereof. In some embodiments, the suspension stabilizing agent and cross-linked mixture are mixed for a time period of about 10 minutes to about 60 minutes. Specific examples of the time period of mixing include about 10 minutes, about 20 minutes, about 30 minutes, about 40 minutes, about 50 minutes, about 60 minutes, and ranges between any two of these values (including endpoints).

At block 106, one or more metallic salts are added to the formed reaction mixture to form a metal nanoparticles-doped polymer bead. Examples of the one or more metallic salts include, but are not limited to, copper nitrate ($Cu(NO_3)_2 \cdot 3H_2O$), silver nitrate ($AgNO_3$), silver chloride (AgCl), copper chloride ($CuCl_2$), copper sulphate ($CuSO_4 \cdot 5H_2O$), silver sulphate ($Ag_2SO_4$), or combinations thereof. Examples of metal nanoparticles that can be incorporated into the polymer beads include, but are not limited to, aluminum (Al), iron (Fe), nickel (Ni), copper (Cu), silver (Ag), cobalt (Co), molybdenum (Mo), gold (Au), platinum (Pt), or combinations thereof. In some embodiments, combinations of metal nanoparticles are incorporated into the beads. Examples of combinations include, but are not limited to, Al and Fe, or Fe and Ni, or Al and Ni, or Cu and Ni, or Cu and Fe, or Cu and Al.

The one or more metallic salts can be added during the suspension polymerization reaction sequentially or simultaneously. In some embodiments, the one or more metallic salts are added at a time difference of about 1 minute to about 10 minutes apart. Specific examples of the time difference include about 1 minute, about 2 minutes, about 3 minutes, about 4 minutes, about 5 minutes, about 6 minutes, about 7 minutes, about 8 minutes, about 9 minutes, about 10 minutes and ranges between any two of these values (including endpoints). The one or more metallic salts can also be added in different ratios to one another. Specific examples of the ratio of a first metallic salt ($Cu(NO_3)_2 \cdot 3H_2O$) and a second metallic salt ($AgNO_3$) include 3:0.1, 1:0.1 and 1:0.3. Other ratios may also be used to affect the final amount of each metal that is incorporated into the porous carbon beads.

After the metallic salts are added, the reaction mixture is continued to be heated. The reaction mixture is stirred continuously and the rate of mixing is kept constant to avoid solidification of the beads. The mixture containing the metallic salts is heated for period of time, for example, a time period of about 1 hour to about 10 hours. Specific examples of the heating time period include about 1 hour, about 2 hours, about 3 hours, about 4 hours, about 5 hours, about 6 hours, about 7 hours, about 8 hours, about 9 hours, about 10 hours and ranges between any two of these values (including endpoints). The mixture is then allowed to cool by incubating the mixture in a cooling bath or by exposing the reaction or reaction vessel to the ambient temperature.

In some embodiments, the metal nanoparticles-doped polymer bead is isolated. The bead can be isolated once the reaction mixture reaches about room temperature using different methods of isolation. In some embodiments, isolating the polymeric bead includes filtering the polymeric bead. In some embodiments, the method also includes fractionating the polymeric bead to produce a composition including a polymeric bead of substantially uniform diameter. Fractionating the beads based upon size allows the beads to be grouped according to a specific size or range of sizes. Any method of fractionating, such as but not limited to, using sieves can be used. Examples of solutions used for washing the isolated bead include, but are not limited to, water, ethanol, methanol, isopropanol, acetone, or the combinations thereof.

At block 108, the metal nanoparticles-doped polymer bead is carbonized and activated to form a porous metal-oxide doped activated carbon bead. The metal nanoparticles-doped polymer bead is carbonized at a sufficient temperature and for a sufficient amount of time. The carbonizing can be performed in a ceramic boat or other suitable container. In some embodiments, the metal nanoparticles-doped polymer bead is carbonized at a temperature of about 900° C. to about 1100° C. Specific examples of the temperature include about 900° C., about 950° C., about 1000° C., about 1050° C., about 1100° C. and ranges between any two of these values (including endpoints). In some embodiments, the metal nanoparticles-doped polymer bead is carbonized for a time period of about 10 minutes to about 120 minutes. Specific examples of the time period include about 10 minute, about 20 minutes, about 30 minutes, about 40 minutes, about 50 minutes, about 60 minutes, about 70 minutes, about 80 minutes, about 90 minutes, about 100 minutes, about 120 minutes and ranges between any two of these values (including endpoints).

In some embodiments, the metal nanoparticles-doped polymer bead is carbonized in an inert atmosphere. Examples of inert gases include, but are not limited to nitrogen ($N_2$), argon (Ar), krypton (Kr), or combinations thereof. In some embodiments, prior to the carbonization, the metal nanoparticles-doped polymer bead is pre-heated from room temperature to the carbonization temperature at a heating rate of about 1° C. per minute to about 5° C. per minute. Specific examples of the heating rate include about 1° C. per minute, about 2° C. per minute, about 3° C. per minute, about 4° C. per minute, about 5° C. per minute and ranges between any two of these values (including endpoints).

In some embodiments, the metal nanoparticles-doped polymer bead is activated after the carbonization to form a porous metal-oxide doped activated carbon bead. The activation of the bead is performed using steam in a furnace. In some embodiments, the metal nanoparticles-doped polymer bead is activated at a temperature of about 800° C. to about 1100° C. Specific examples of the temperature include about 800° C., about 900° C., about 1000° C., about 1100° C. and ranges between any two of these values (including endpoints). In some embodiments, the carbonized bead is activated for a time period of about 10 minutes to about 120 minutes. Specific examples of the time period include about 10 minutes, about 20 minutes, about 30 minutes, about 40 minutes, about 50 minutes, about 60 minutes, about 70 minutes, about 80 minutes, about 90 minutes, about 100 minutes, about 120 minutes and ranges between any two of these values (including endpoints).

At block 110, the metal-oxide doped activated carbon bead is reduced to form a metal nanoparticles-doped porous carbon bead. In some embodiments, the metal nanoparticles-doped porous carbon bead is subjected to hydrogen atmosphere to convert the oxides of metal to their pure metallic state. The metal nanoparticles-doped porous carbon bead can be subjected to hydrogen at a temperature of about 325° C. to about 375° C. In some embodiments, a flow rate of hydrogen is about 125 cc per minute to about 175 cc per minute. Moreover, once the reduction to pure metallic state is completed, the metal nanoparticles-doped porous carbon bead is cooled to room temperature under an inert atmosphere.

In this example, the one or more metallic salts enhance the porosity of the polymer bead. In some embodiments, the metal nanoparticles-doped porous carbon bead has a microporosity of about 75% to about 90%. Specific examples of the microporosity include about 75%, about 80%, about 85%, about 90%, and ranges between any two of these values (including endpoints).

In one example, the microporosity of the metal nanoparticles-doped porous carbon bead can be determined based on nitrogen ($N_2$) adsorption and desorption. In this embodiment, the nitrogen ($N_2$) adsorption and desorption are carried out at a temperature of about 77 K. Further, the total surface area and pore volume of the materials can be determined from the nitrogen adsorption/desorption and multi-point isotherms, using the Brunauer-Emmett-Teller (BET) equation. Moreover, micro and meso pore volumes can be determined using density functional theory and Barret-Joyner-Halenda technique, respectively.

In one example embodiment, metal nanoparticles-doped porous carbon beads are formed using the process of FIG. 1. As discussed above, a variety of metal nanoparticles can be incorporated into the bead. Examples of the metal nanoparticles include, but are not limited to, aluminum (Al), iron (Fe), nickel (Ni), copper (Cu), silver (Ag), cobalt (Co), molybdenum (Mo), gold (Au), platinum (Pt), or combinations thereof. In one example, the porous carbon bead is doped with at least one of silver (Ag) and copper (Cu) nanoparticles.

In one example embodiment, the porous carbon bead is doped with both silver and copper nanoparticles. In this example, the loading of silver is about 1 milligram (mg) to about 6 mg per gram of the porous carbon bead. Specific examples of silver loading include about 1 mg, about 2 mg, about 3 mg, about 4 mg, about 5 mg, about 6 mg per gram of the porous carbon bead and ranges between any two of these values (including endpoints). In this example, loading of copper is about 5 mg to about 25 mg per gram of the porous carbon bead. Specific examples of copper loading include about 5 mg, about 10 mg, about 15 mg, about 20 mg, about 25 mg per gram of the porous carbon bead and ranges between any two of these values (including endpoints).

Further, the metal nanoparticles-doped porous carbon beads synthesized using the process described above can have a surface area of about 750 $m^2/g$ to about 1100 $m^2/g$. Specific examples of the surface area of the beads include about 750 $m^2/g$, about 800 $m^2/g$, about 850 $m^2/g$, about 900 $m^2/g$, about 950 $m^2/g$, about 1000 $m^2/g$, about 1050 $m^2/g$, about 1100 $m^2/g$ and ranges between any two of these values (including endpoints).

In this example, the addition of copper to the carbonized polymer beads during suspension polymerization reaction substantially increases the porosity of the resulting metal nanoparticles-doped porous carbon beads. In some examples, the metal nanoparticles-doped porous carbon beads have a micro-porosity of about 75% to about 90%. Specific examples of the microporosity include about 75%, about 80%, about 85%, about 90%, and ranges between any two of these values (including endpoints). In some examples, an average diameter of the silver and copper nanoparticles is about 10 nanometers (nm) to about 200 nm Specific examples of diameter include about 10 nm, about 40 nm, about 80 nm, about 120 nm, about 160 nm, about 200 nm and ranges between any two of these values (including endpoints).

The metal nanoparticles-doped porous carbon bead described above has substantially uniform dispersion of single or bi-nanometals (for example, silver and copper) within their micro/meso pores and exhibit antibacterial activities. In the beads doped with both silver and copper, the overall quantity of silver and copper included in the metal nanoparticles-doped porous carbon beads is substantially less than that of the single metal (Ag or Cu) required for preparing metal doped carbon beads having similar antibacterial properties. In particular, the addition of copper nanoparticles to the beads significantly reduces the quantity of silver required to prepare the bi-metallic beads while maintaining the same performance as that of single metal incorporated beads. Thus, addition of Cu enhances the antibacterial activity of the beads and increases the porosity of the beads thereby increasing the accessibility of Ag-active sites dispersed in the beads to the bacteria. In certain embodiments, the metal nanoparticles-doped porous carbon beads can inhibit bacteria from a sample for a time period of about 100 hours to about 130 hours.

Figure 2:
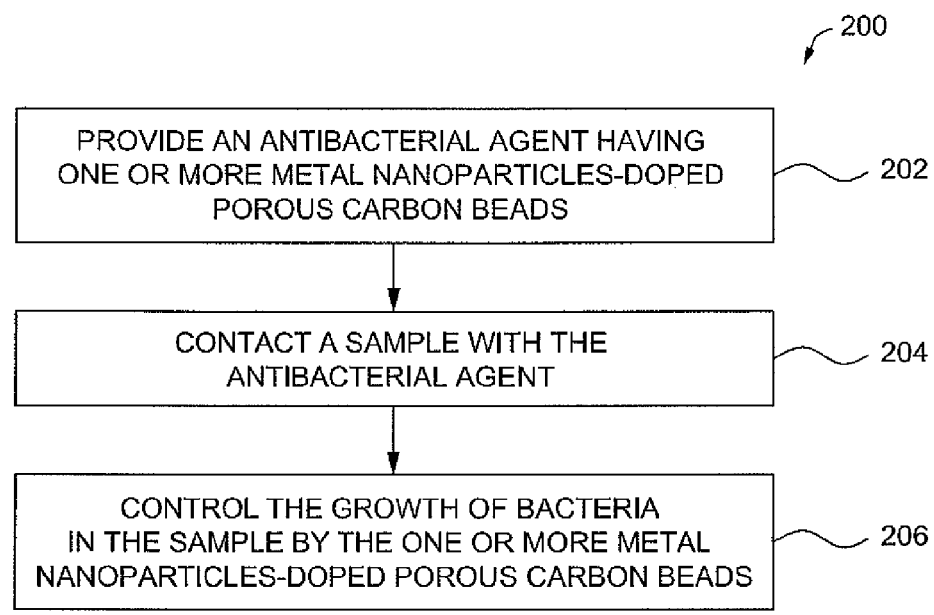
FIG. 2 is an example flow diagram of an embodiment of a method of inhibiting bacteria in a sample.

Referring now to FIG. 2, an example flow diagram 200 of an embodiment of a method of inhibiting bacteria in a sample is illustrated. At block 202, an antibacterial agent is provided. In this example, the antibacterial agent includes one or more metal nanoparticles-doped porous carbon beads. The one or more porous carbon beads are doped with silver and copper nanoparticles. At block 204, a sample having bacteria is contacted with the antibacterial agent.

The growth of bacteria in the sample is controlled by the one or more metal nanoparticles-doped porous carbon beads (block 206). In one example, the bacteria are gram-positive bacteria. In another example, the bacteria are gram-negative bacteria. In one example embodiment, the metal nanoparticles-doped porous carbon bead inhibits bacteria from the sample for at least about 100 hours. In one example embodiment, the metal nanoparticles-doped porous carbon bead inhibits bacteria from the sample for a time period of about 100 hours to about 130 hours. Specific examples of the inhibition time period include about 100 hours, about 105 hours, about 110 hours, about 115 hours, about 120 hours, about 125 hours, about 130 hours and ranges between any two of these values (including endpoints).

In some embodiments, water filters having the antibacterial agent provided. In this example, the antibacterial agent includes one or more metal nanoparticles-doped porous carbon beads. The one or more porous carbon beads can be doped with silver and copper nanoparticles. The water filter can also include other materials such as activated charcoal, membranes, or other materials commonly found in filters used to filter drinking water. In some embodiments, the water filter is a filter that is attached directly to a faucet such that the water exiting the faucet passes through the filter. In some embodiments, the filter is placed upstream of the faucet. The filter can be, for example, be placed where the water enters a supply line in a home or business. In some embodiments, the filter is in a water pumping station. Filters can be configured depending upon the use and where the water is treated

EXAMPLES

The present invention will be described below in further detail with examples and comparative examples thereof, but it is noted that the present invention is by no means intended to be limited to these examples.

Example 1

Figure 3:
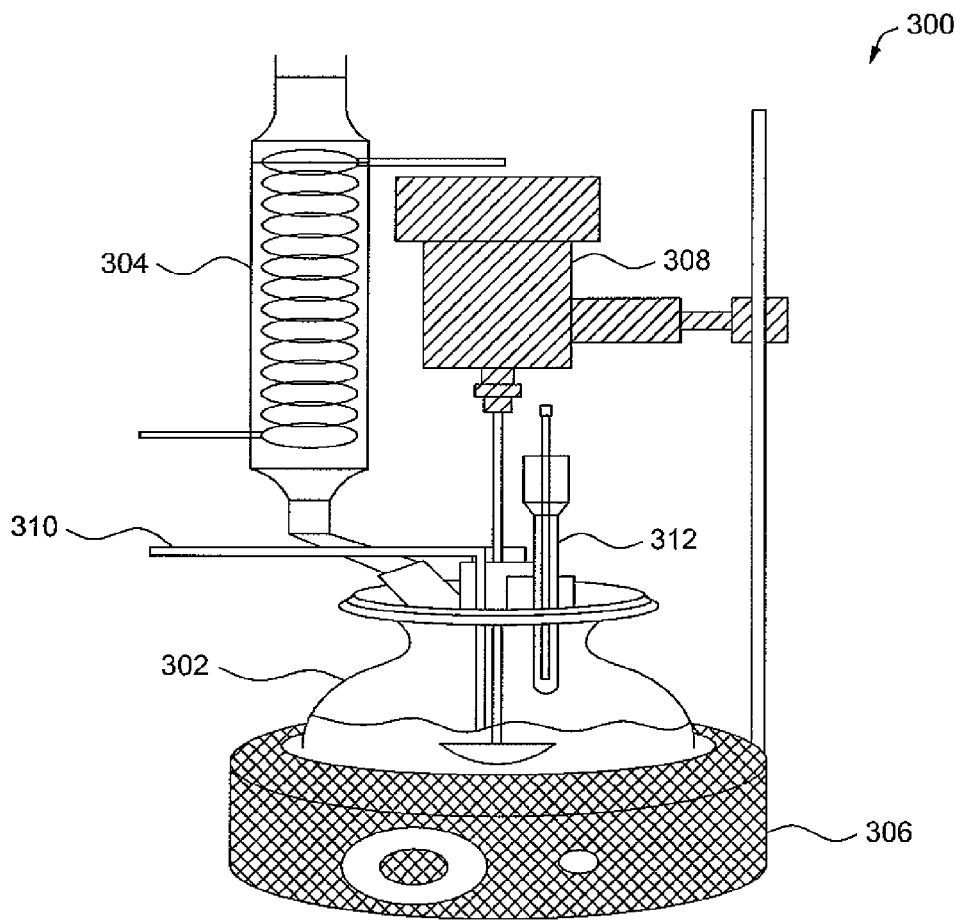
FIG. 3 is an example apparatus used for forming metal nanoparticles-doped porous carbon beads by suspension polymerization reaction.

Configuration of Experimental Set-Up Used for Forming Metal Nanoparticles-Doped Porous Carbon Beads:

FIG. 3 illustrates an example apparatus 300 used for forming metal nanoparticles-doped porous carbon beads by suspension polymerization reaction. As illustrated, the apparatus 300 included a round bottom three-neck glass flask 302 (having a capacity of about 2 liters (1)) attached with a reflux-condenser 304. The glass flask 302 contained the reaction mixture for forming the polymer bead. The glass flask 302 was mounted over a heating mantle 306 and was equipped with a stirrer 308. Moreover, the apparatus 300 included an inlet 310 to supply inert gas that formed a blanket of inert atmosphere over the reaction mixture in the glass flask 302. A thermometer 312 was employed to monitor the temperature of the reaction mixture in the glass flask 302 during the reaction.

Example 2

Formation of Metal Nanoparticles-Doped Porous Carbon Beads:

The apparatus of Example 1 was used to form the metal nanoparticles-doped porous carbon beads. A reaction mixture was formed in the glass flask 302 by mixing about 45 grams (g) of phenol, about 55 cubic centimeters (cc) of formaldehyde, and about 1.5 milliliters (ml) of TEA used as monomer, solvent, and catalyst respectively. The reaction mixture was stirred using the stirrer 308 at a temperature of about 35° C. for a time period of about 8 hours to get a homogeneous reaction mixture. The speed of the stirrer 308 was maintained at about 120 revolutions per minute (rpm). Further, about 200 ml of de-ionized (DI) water was added to the homogeneous reaction mixture and the speed of the stirrer 308 was increased to about 350 rpm.

Further, about 3.5 g of hexamine (used as a cross-linking agent) was added to the reaction mixture after a time period of about 30 minutes. The solution was heated at a rate of about 3° C. per minute until the temperature of the reaction mixture reached to about 105° C. After a time period of about 15 minutes, about 3 g of PVA (used as a suspension stabilizing agent) was added to the reaction mixture.

After about 30 minutes of adding PVA, a gel formation was observed and silver nitrate ($AgNO_3$) and copper nitrate ($Cu(NO_3.3H_2O)$) were added to the reaction mixture in a sequential manner within a time span of about 4 minutes. The metallic salts ($AgNO_3$ and $Cu(NO_3.3H_2O)$) were added in different proportions. The proportions included about 0.1 g of $AgNO_3$ and about 3 g of ($Cu(NO_3.3H_2O)$), about 0.3 g of $AgNO_3$ and about 1 g of ($Cu(NO_3.3H_2O)$), about 0.2 g of $AgNO_3$ and about 2 g of ($Cu(NO_3.3H_2O)$) respectively. Subsequently, sodium dodecyl sulfate (SDS) used as a surfactant was added to the reaction mixture to prevent agglomeration of Cu and Ag ions and to create a uniform dispersion of metallic salts in the reaction mixture.

The reaction mixture was continued to be heated after the addition of metallic salts. The speed of the stirrer 308 was maintained at about 350 rpm to prevent lumps formation or agglomeration of the beads. The heating was stopped after a time period of about 1.5 hours and the reaction mixture was allowed to cool in still air. Once the temperature of the reaction products reached a temperature of about 35° C., the products were filtered to separate solids from the residual liquid. The filtered products were washed about three times with distilled water, methanol and acetone respectively. The formed metal nanoparticle-doped polymer beads were then sieved and a yield of about 40 g was obtained.

The produced metal nanoparticle-doped polymer beads were carbonized at a temperature of about 850° C. for a time period of about 1 hour under nitrogen ($N_2$) atmosphere at about 150 cc per minute. A horizontal tubular furnace was used for the carbonization. A perforated stainless steel (SS) boat was used to hold the produced metal nanoparticle-doped polymer beads. Prior to the carbonization, the beads were pre-heated from room temperature to the carbonization temperature at a heating rate of about 5° C. per minute. Further, activation was carried out at a temperature of about 800° C. using steam as the activation agent in the same furnace-boat assembly to form porous metal-oxide doped activated carbon beads. The flow rate of $N_2$ was subsequently reduced to about 120 cc per minute.

The metal-oxide doped activated carbon beads were then subjected to hydrogen atmosphere at rate of about 150 cc per minute at a temperature of about 350° C. for a time period of about 1 hour to reduce the oxides of metals into their respective pure metallic state. The beads were allowed to cool to room temperature under $N_2$ flow. The yield of the carbonized and activated bi-metal beads varied in the range of about 50% to about 60% of the initial weight of the polymeric beads.

Example 3

Characterization of the Metal Nanoparticles-Doped Porous Carbon Beads:

The metal nanoparticles-doped porous carbon beads synthesized using the process described in Example 2 were characterized using atomic absorption analysis (AAS) to determine the metal loadings. The analysis showed the loading of each metal (Ag and Cu) varying between a range of about 3 mg/g to about 18 mg/g of the materials, depending on the relative amounts of the respective metallic salts used in the synthesis. The Brunauer-Emmett-Teller (BET) area and pore size distribution (PSD) analysis was also carried out to determine the total surface area and the PSD. It was observed from the analysis that the BET area was in a range of about 750 $m^2/g$ to about 1100 $m^2/g$. Further, the Ag impregnated beads had relatively lesser BET area than that of Cu impregnated beads.

Figure 4:
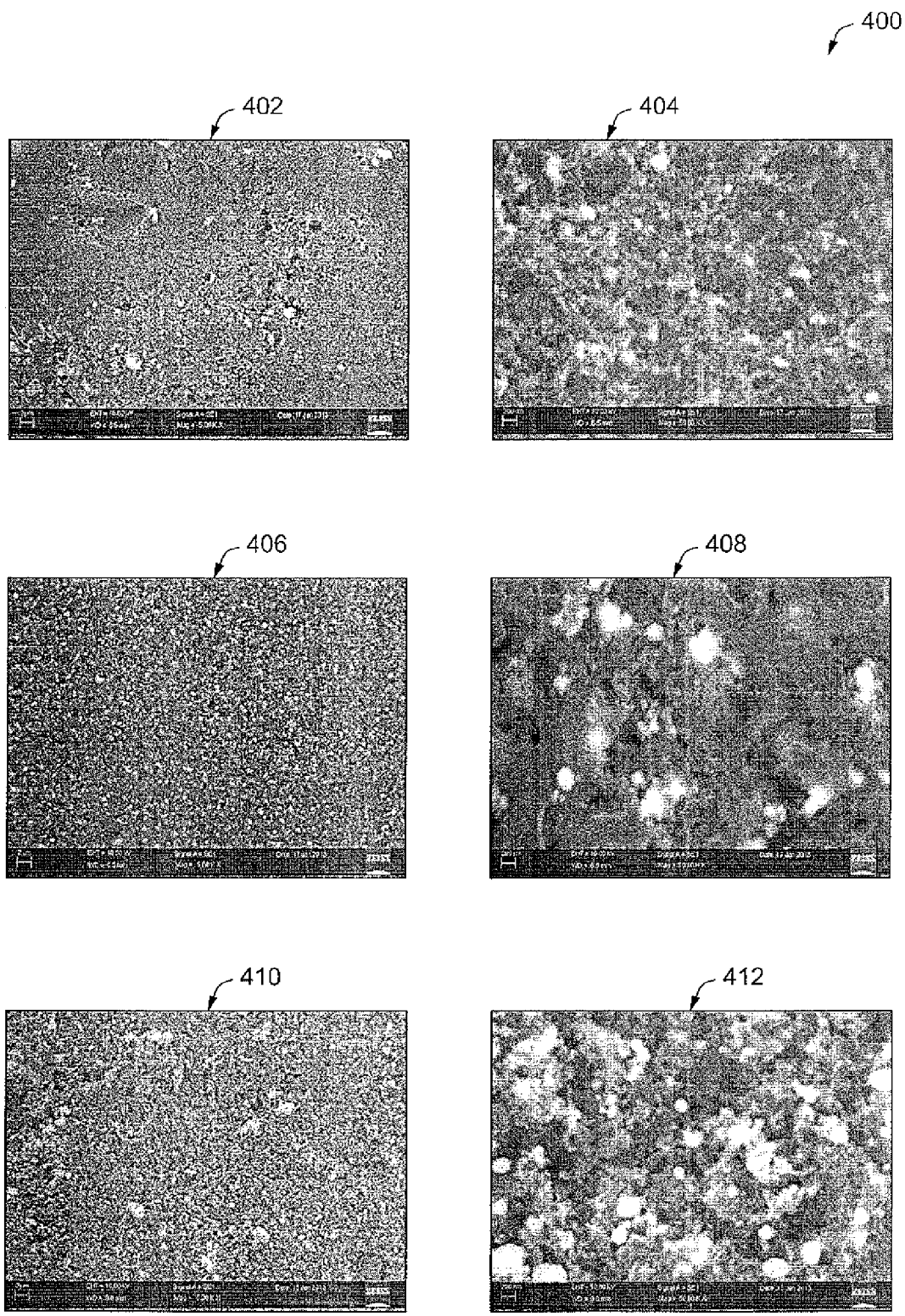
FIG. 4 illustrates example scanning electron microscopy (SEM) images of single and bi-metal nanoparticles-doped porous carbon beads.

FIG. 4 illustrates example scanning electron microscopy (SEM) images 400 of single and bi-metal nanoparticles-doped porous carbon beads of Example 2. Here, SEM images of Ag nanoparticles-doped porous carbon beads obtained at a resolution of about 2 micrometers and about 200 nanometers are represented by reference numerals 402 and 404 respectively. Further, SEM images of Cu nanoparticles-doped porous carbon beads obtained at a resolution of about 2 micrometers and about 200 nanometers are represented by reference numerals 406 and 408 respectively. In addition, SEM images of Ag/Cu nanoparticles-doped porous carbon beads obtained at resolution of about 2 micrometers and about 200 nanometers are represented by reference numerals 410 and 412 respectively.

As can be seen from the images, the external surface of the beads was observed to be porous having micro-mesopores. Further, Ag nanoparticles-doped porous carbon beads were observed to be relatively lesser porous as compared to the Cu nanoparticles-doped porous carbon beads. Moreover, the porosity of the Ag/Cu nanoparticles-doped porous carbon beads was observed to be in between that of the Ag nanoparticles-doped porous carbon beads and the Cu nanoparticles-doped porous carbon beads. It was observed that the distribution of the Ag and Cu nanoparticles on an external surface of the porous carbon beads was uniform and the size of the Ag and Cu nanoparticles on the surface of the beads was observed to be in the range of about 10 nm to about 200 nm Example 4

Antibacterial Performance of the Metal Nanoparticles-Doped Porous Carbon Beads:

The metal nanoparticles-doped porous carbon beads of Example 2 were used for inhibition of bacteria in a sample. The antibacterial activity test of the metal nanoparticles-doped porous carbon beads was performed for gram-negative *E. coli* and gram-positive *S. aureus* bacteria using the plate counting method. Here, about 1 ml of bacterial Lysogeny broth (LB) was diluted with about 50 ml of sterilized DI water in several Erlenmeyer flasks. Further, about 0.1 g of each of Ag nanoparticles-doped porous carbon beads, Cu nanoparticles-doped porous carbon beads and Ag/Cu nanoparticles-doped porous carbon beads were added to the broth. The bacteria count was initially measured to be about $10^7$ per ml to about $10^8$ per ml.

The flasks containing the bacterial broth and the each of the Ag nanoparticles-doped porous carbon beads, Cu nanoparticles-doped porous carbon beads and Ag/Cu nanoparticles-doped porous carbon beads were maintained in a shaking incubator at a temperature of about 37° C. at a speed of about 120 rpm. Samples of about 1 ml solution were obtained from each flask every 12 hours and were used for further analysis. The tests were carried out for a time period of about 72 hours.

Figure 5:
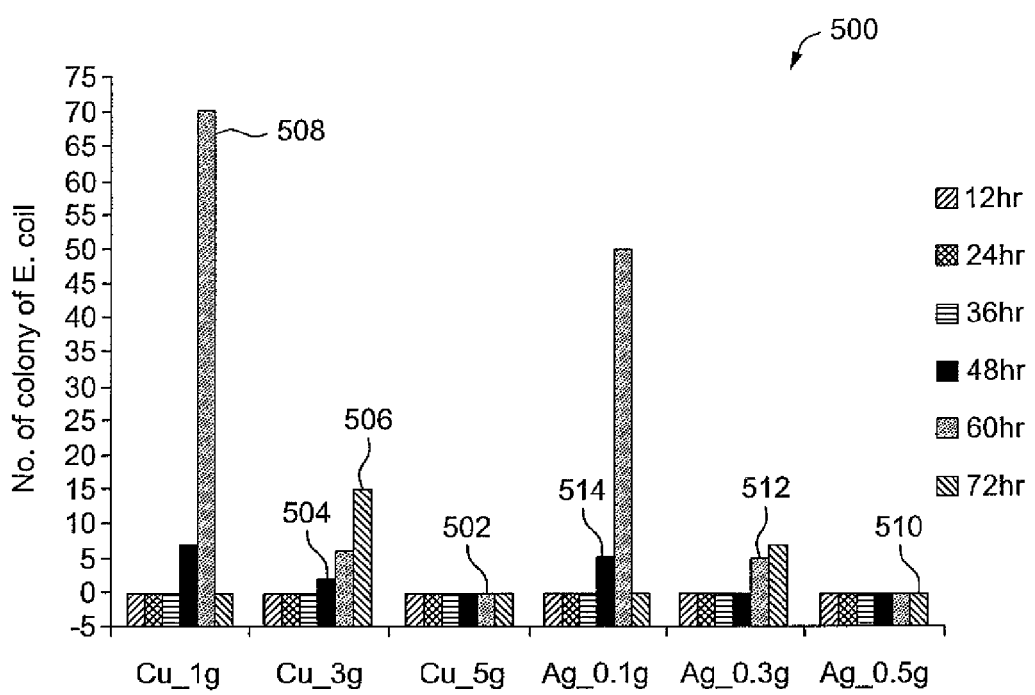
FIG. 5 is an example graphical representation of antibacterial performance of single metal (Cu or Ag) nanoparticles-doped porous carbon beads.
Figure 6:
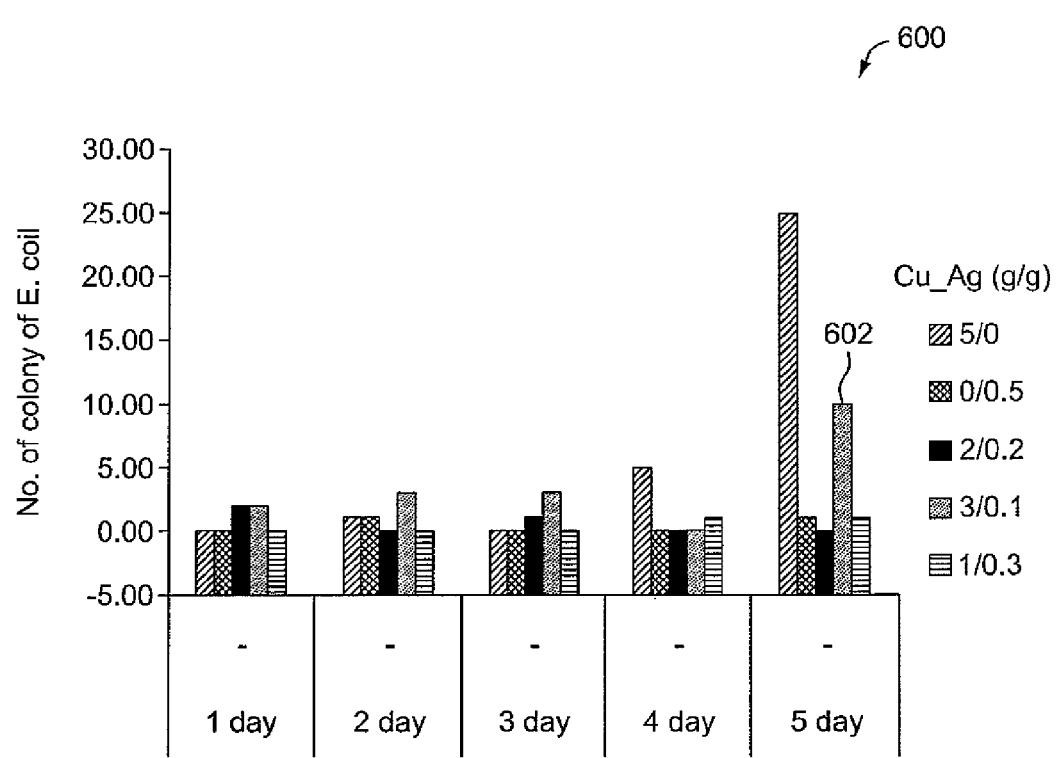
FIG. 6 is an example graphical representation of antibacterial performance of bi-metals (Cu and Ag) nanoparticles-doped porous carbon beads.

FIG. 5 and FIG. 6 are graphical representations 500 and 600 of antibacterial performance of the metal nanoparticles-doped porous carbon beads having single metal (Cu or Ag) nanoparticles-doped porous carbon beads and bi-metals (Cu and Ag) nanoparticles-doped porous carbon beads respectively. Here, the number of colonies of *E. coli* bacteria grown on an LB agar plate using the samples of Example 5 were measured.

As can be seen from the profile 500, an increase in amounts of either metal (Cu or Ag) in the porous carbon beads suppressed the growth of the bacteria over a relatively longer period. Further, the growth of bacteria was suppressed for a time period of about 72 hours by the Cu nanoparticles-doped porous carbon beads prepared from about 5 g of the metallic salt as indicated by reference numeral 502. However, some bacteria colonies started to appear in a time period of about 48 hours when Cu nanoparticles-doped porous carbon beads prepared from relatively lesser (about 3 g) of metallic salt were used in the sample (as represented by reference numeral 504). In the time period of about 72 hours, the numbers of colonies were observed to have increased to about 15, as represented by reference numeral 506.

A significant number of colonies appeared after a time period of about 48 hours for Cu nanoparticles-doped porous carbon beads prepared from about 1 g of copper salt only. Moreover, the number of colonies substantially increased after a time period of about 72 hours as indicated in the plot by reference numeral 508. The results for the antibacterial performance of the single metal (Cu or Ag) nanoparticles-doped porous carbon beads are provided in Table 1.

TABLE 1

| Sample | Number of colony of E. Coli | | | | | |
|---|---|---|---|---|---|---|
| | 12 hours | 24 hours | 36 hours | 48 hours | 60 hours | 72 hours |
| Cu_1 g | 0 | 0 | 0 | 7 | 70 | — |
| Cu_3 g | 0 | 0 | 0 | 2 | 6 | 15 |
| Cu_5 g | 0 | 0 | 0 | 0 | 0 | 0 |
| Ag_0.1 g | 0 | 0 | 0 | 5 | 50 | — |
| Ag_0.3 g | 0 | 0 | 0 | 0 | 5 | 7 |
| Ag_0.5 g | 0 | 0 | 0 | 0 | 0 | 0 |

It was also observed from these results that substantially less quantity of Ag was sufficient for suppressing the growth of the bacteria colony. Here, no growth was observed for a time period of about 72 hours when beads prepared from 0.5 g of Ag salt were used, as represented by reference numeral 510. The bacteria growth started occurring in time period of about 60 hours when beads prepared from 0.3 g of Ag salt were used, as represented by reference numeral 512. Further, the beads prepared from about 0.1 g of Ag salt were observed to be unable to suppress the growth after a time period of about 48 hours and the number of bacteria was substantially large, as represented by reference numeral 514.

As can be seen from profile 600, similar antibacterial performance was observed using the bi-metals (Cu and Ag) nanoparticles-doped porous carbon beads that were prepared from substantially less than half of the amount of the corresponding single metallic salt. It was also observed that growth of bacteria significantly increased when the amount of Ag salt was halved to about 0.1 g and that of Cu salt increased to about 3 g in the porous carbon beads (as represented by reference numeral 602). Thus, the performance of the bi-metal (Cu and Ag) nanoparticles-doped porous carbon beads containing about 3 g of Cu and about 0.1 g of Ag salts is intermediate between that of the single metal nanoparticles-doped porous carbon beads prepared using the same amount of the respective metal. The corresponding results for the antibacterial performance of the bi-metal beads are provided in Table 2.

TABLE 2

| Sample | Weight of Cu:Ag (g) | Number of colonies of E. Coli | | | | |
|---|---|---|---|---|---|---|
| | | Day-1 | Day-2 | Day-3 | Day-4 | Day-5 |
| Cu | 5/0 | 0 | 1 | 0 | 5 | 25 |
| Ag | 0/0.5 | 0 | 1 | 0 | 0 | 1 |
| Cu_Ag | 2/0.2 | 2 | 0 | 1 | 0 | 0 |
| Cu_Ag | 3/0.1 | 2 | 3 | 3 | 5 | 10 |
| Cu_Ag | 1/0.3 | 0 | 0 | 1 | 0 | 1 |

The antibacterial performance of the bi-metal (Cu and Ag) nanoparticles-doped porous carbon beads formed using the process described above was compared with the antibacterial performance of other available antibacterial agents. The comparison of the antibacterial performance is provided in Table 3.

TABLE 3

| Material | Bacteria | Initial no. of bacteria per ml | % Inhibition | Time of microbial test |
|---|---|---|---|---|
| Ag—Cu nanoparticles-doped porous carbon beads | E. coli and S. aureus | $10^7$-$10^8$ | 100 | 120 hours |
| AgNO$_3$ and sodium linoleate | S. aureus, S. basillus | $10^5$-$10^6$ | 97 | 24 hours |
| Ag—Cu-agarose composite | E. coli | n/a | 50-100 (Ag) 100 (Cu) | 12 hours |
| Hydrogel-Ag-nanocomposite | E. coli | n/a | — | 24 hours |
| Ag-nanoparticle in hyperbranched polyamine | Bacillus subtillis and S. aureus | n/a | Strong antibacterial effect | 24 hours |
| PVA-Ag-composite | E. coli and S. aureus | $10^6$-$10^7$ | Excellent antibacterial effect | 48 hours |
| Ag-hydrosol | E. coli | $10^5$ | 70-100 | 24 hours |
| Ag-nanoparticle | E. coli and S. aureus etc. | $10^5$-$10^6$ | 90 | 24 hours |
| Cu nanoparticle on SiO$_2$ surface | E. coli and S. aureus etc. | n/a | Strong antibacterial effect | 24 hours |
| Ag nanoparticle containing silica bead | E. coli | $(5\text{-}6) * 10^6$ | 100 | 20 minutes |
| Ag doped TiO$_2$ film and UV radiation | E. coli and S. aureus etc. | $2 * 10^9$ | 69-99.9 | 2-6 hours |
| Ag-hydroxyapatite | E. coli and S. aureus etc. | $10^5$ | 100 | 24 hours |

As can be seen from the above comparison, the antibacterial performance of bi-metal (Cu and Ag) nanoparticles-doped porous carbon beads is significantly better than the other materials including the materials that were prepared by transferring AgNO$_3$ and (Cu(NO$_3$)$_2$.3H$_2$O) to solid surfaces. For example, a majority of materials listed above when used with water sample with about $10^4$-$10^7$ bacteria per ml of the sample, the growth of bacteria was inhibited for not more than 48 hours. However, the bi-metal (Cu and Ag) nanoparticles-doped porous carbon beads used as an antibacterial agent achieved the inhibition of bacteria for about 120 hours.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims.

The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation, no such intent is present.

For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general, such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.).

It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

As will be understood by one skilled in the art, for any and all purposes, such as in terms of providing a written description, all ranges disclosed herein also encompass any and all possible sub ranges and combinations of sub ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc.

As will also be understood by one skilled in the art all language such as "up to," "at least," "greater than," "less than," and the like include the number recited and refer to ranges which can be subsequently broken down into sub ranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A metal nanopartieles-doped porous carbon head having an average size of about 0.4 mm to about 0.6 mm, wherein a porous carbon bead is doped with silver and copper nanoparticles and a loading of silver is about 1 milligram (mg) to about 6 mg per gram (g) of the porous carbon bead and a loading of copper is about 5 mg to about 25 mg per gram (g) of the porous carbon bead, wherein the metal nanoparticles-doped porous carbon bead is an antibacterial agent and provides 100% inhibition of bacteria in a sample for a time period of about 100 hours to about 130 hours, and wherein the bacteria are gram-positive bacteria, gram-negative bacteria, or combinations thereof.

2. The metal nanopartieles-doped porous carbon bead of claim 1, wherein the metal nancparticles-doped porous carbon bead has a surface area of about 750 $m^2/g$ to about 1100 $m^{2/g}$.

3. The metal nanoparticles-doped porous carbon bead of claim 1, wherein the metal nanoparticles-doped porous carbon bead has a microporosity of about 75% to about 90%.

4. The metal nanoparticles-doped porous carbon bead of claim 1, wherein the silver and copper nanoparticles have an average diameter of about 10 nanometers (nm) to about 200 nm.

5. An antibacterial agent for inhibiting bacteria, the antibacterial agent comprising one or more metal nanopartieles-doped porous carbon beads, wherein the one or more porous carbon beads are doped with silver and copper nanoparticles and a loading of silver is about 1 milligram (mg) to about 6 mg per gram (g) of the porous carbon beads and a loading of copper is about 5 mg to about 25 mg per gram (g) of the porous carbon beads, wherein the silver and copper nanoparticles are substantially uniformly dispersed within pores of the porous carbon bead and provides 100% inhibition of bacteria in a sample for a time period of about 100 hours to about 130 hours, and wherein the bacteria are gram-positive bacteria, gram-negative bacteria, or combinations thereof.

6. The antibacterial agent of claim 5, wherein the antibacterial agent is configured for use in a water filter for controlling growth of the bacteria in water.

* * * * *

UNITED STATES PATENT AND TRADEMARK OFFICE
CERTIFICATE OF CORRECTION

PATENT NO. : 9,844,222 B2
APPLICATION NO. : 14/462580
DATED : December 19, 2017
INVENTOR(S) : Verma et al.

It is certified that error appears in the above-identified patent and that said Letters Patent is hereby corrected as shown below:

In the Specification

In Column 6, Line 63, delete "200 nm" and insert -- 200 nm. --, therefor.

In the Claims

In Column 14, Line 22, in Claim 1, delete "metal nanopartieles-doped" and insert -- metal nanoparticles-doped --, therefor.

In Column 14, Line 22, in Claim 1, delete "carbon head" and insert -- carbon bead --, therefor.

In Column 14, Line 25, in Claim 1, delete "nanoparticles and" and insert -- nanoparticles, and --, therefor.

In Column 14, Line 34, in Claim 2, delete "nanopartieles-doped" and insert -- nanoparticles-doped --, therefor.

In Column 14, Line 35, in Claim 2, delete "nancparticles-doped" and insert -- nanoparticles-doped --, therefor.

In Column 14, Lines 36-37, in Claim 2, delete "1100 $m^{2/g}$" and insert -- 1100 $m^2/g$. --, therefor.

In Column 14, Lines 46-47, in Claim 5, delete "nanopartieles-doped" and insert -- nanoparticles-doped --, therefor.

Signed and Sealed this
Thirty-first Day of July, 2018

Andrei Iancu
*Director of the United States Patent and Trademark Office*